United States Patent [19]

Collins et al.

[11] 4,382,795
[45] May 10, 1983

[54] THERAPEUTIC AID FOR THE HANDICAPPED

[76] Inventors: Ellwood J. Collins; Helen M. Collins, both of 2020 Gregg St., Carson City, Nev. 89701

[21] Appl. No.: 235,961

[22] Filed: Feb. 19, 1981

[51] Int. Cl.³ .................... G09B 5/00; A63B 23/00
[52] U.S. Cl. ........................ 434/258; 128/26; 272/67; 272/DIG. 5
[58] Field of Search .............. 434/258, 260, 236; 272/DIG. 5, DIG. 6; 128/67, 26

[56] References Cited

U.S. PATENT DOCUMENTS

| | | | |
|---|---|---|---|
| D. 187,218 | 2/1960 | McHugh | 434/258 X |
| 2,870,549 | 1/1959 | Crane | 434/236 |
| 3,346,968 | 10/1967 | Dellinger | 434/258 |
| 3,538,620 | 11/1970 | Kohner et al. | 434/258 |
| 3,654,710 | 4/1972 | Barnard | 434/258 |
| 3,657,456 | 4/1972 | Kozak | 434/258 |

Primary Examiner—William H. Grieb
Attorney, Agent, or Firm—Harvey B. Jacobson

[57] ABSTRACT

A teaching machine for improving hand and eye coordination, as well as muscle development in the fingers, wrists and forearms of handicapped individuals includes a plurality of various types of electrical switches which are operably associated with a color coding on a viewing panel and may be operated to control a color display. Additionally, several mechanical exercising devices which are adjustably variable in tension are included as a part of the machine, while hand and eye coordination is accomplished by the matching of the particular switches and colored lights on the viewing panel.

14 Claims, 11 Drawing Figures

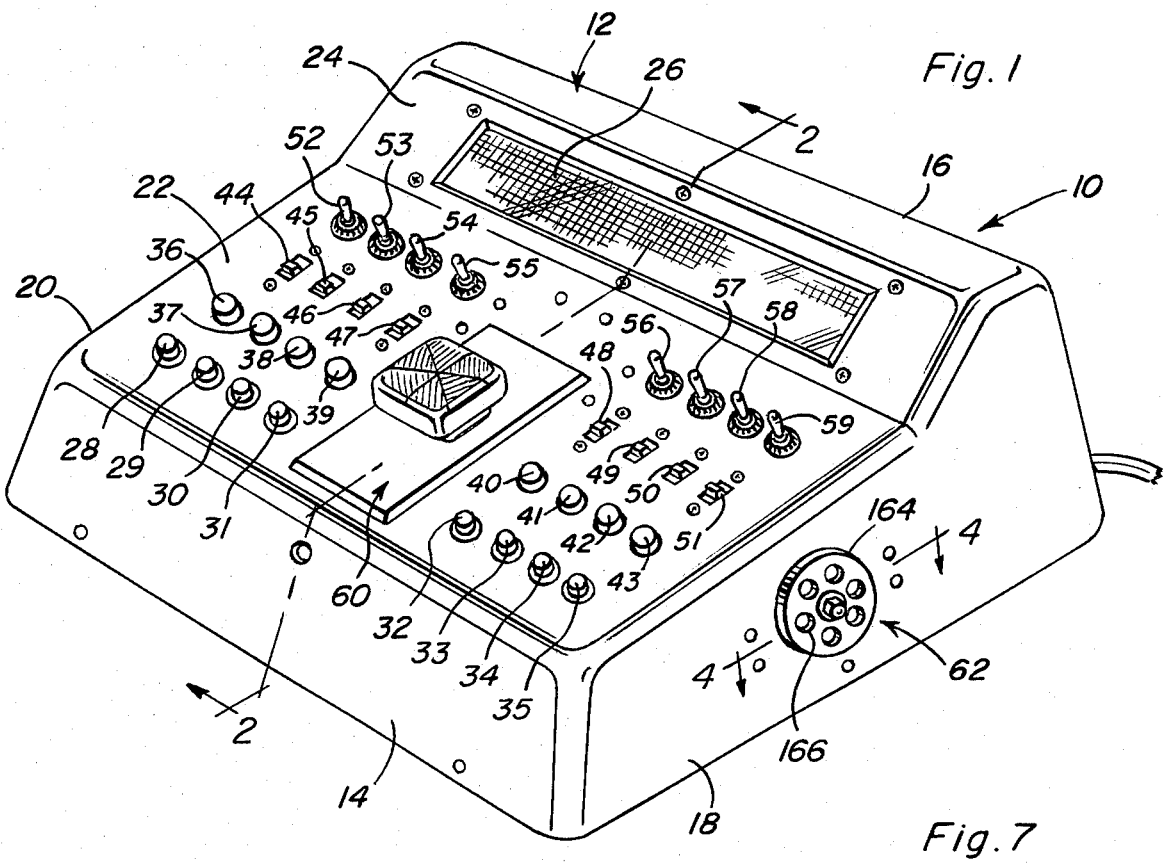

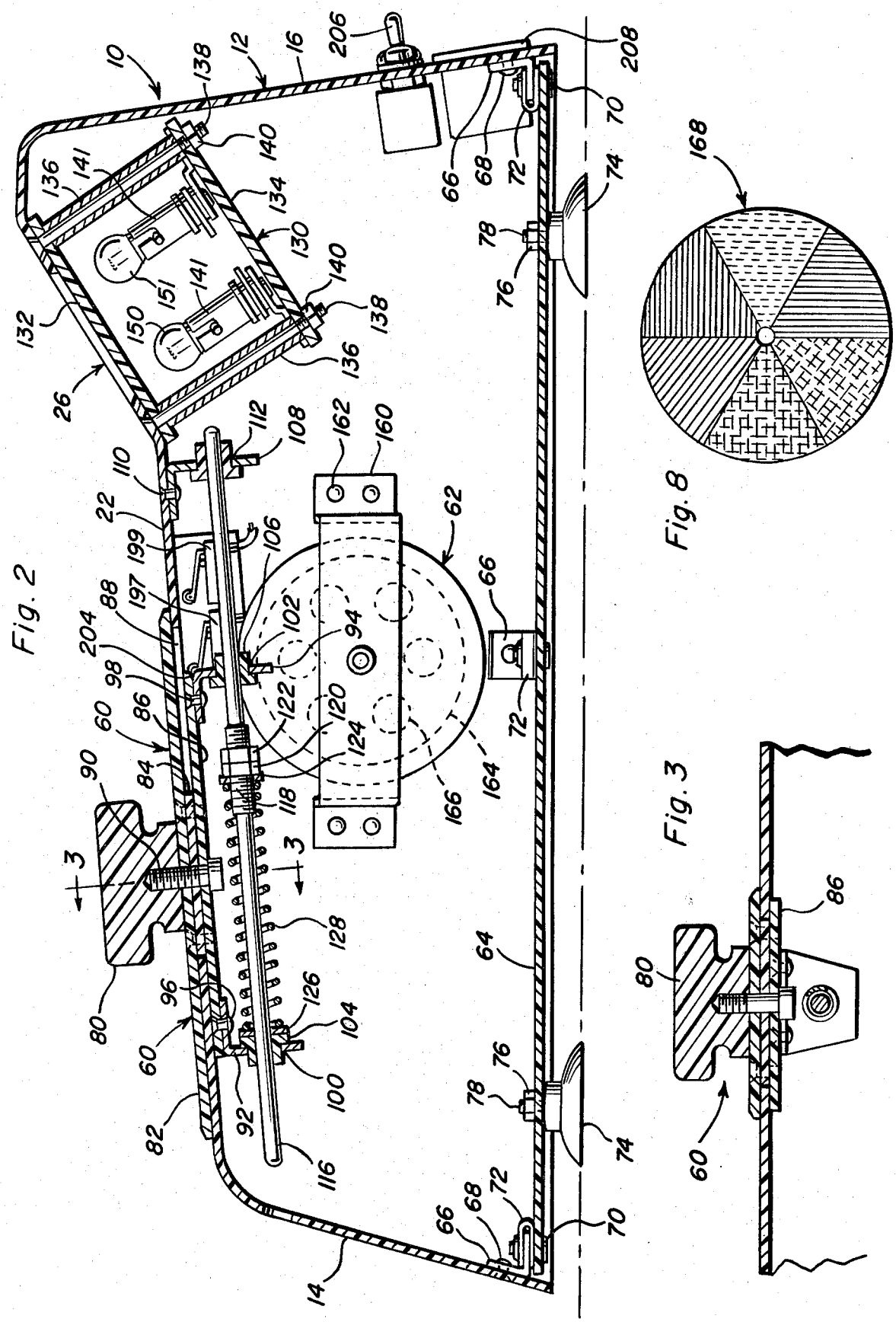

THERAPEUTIC AID FOR THE HANDICAPPED

BACKGROUND OF THE INVENTION

1. Field of the Invention

The present invention relates to teaching machines and more particularly pertains to a therapeutic aid for the handicapped which employs a plurality of switches, lights and muscle exercising devices to facilitate improvement in muscle control, as well as in hand and eye coordination.

2. Description of the Prior Art

There exists a continuing need for easily transportable and operational teaching devices that assist handicapped individuals to regain the use of their motor reflexes and coordination. In this respect, there has been a number of attempts in the prior art to provide such devices. For example, U.S. Pat. No. 3,654,710, issued to Barnard on Apr. 11, 1972, discloses a selectively illuminable toy which may be utilized to teach hand and eye coordination for children. In this regard, there is provided a control knob operably associated with a selected number of distinctive illuminable stations on a display board in such a way that the stations are sequentially illuminated and darkened by a movement of the knob. In one form of the Barnard device, a rotary switch coupled to the knob sequentially connects power from a battery to a separate light bulb at each station as the knob is turned, and indicia provided on the display board serves to correlate each station with a knob setting. In another form of the Barnard device, a light bulb is mounted on a radial arm secured to the knob so as to rotate to each station as the knob is turned, and in yet another form of the invention, light from a common light bulb is transmitted to each station via a lightconductive rod coupled to the knob. As such, the Barnard device allows a user to coordinate a rotary switch position with a particular light so as to facilitate hand and eye coordination as above discussed. However, the Barnard teaching machine makes no use of a plurality of different switches which may be coordinated to illuminate particular lights, nor is there any exercising devices associated therewith.

Similarly, in U.S. Pat. No. 3,657,456, issued to Kozak on Apr. 18, 1972, there is disclosed a device for teaching coordination or rhythm which includes a plurality of figures illuminable in varying cycles of equally spaced intervals, a plurality of illuminable lamps associated with each of the fingers and a multiplicity of switches for the lamps so that any or all of the lamps associated with the fingers may be illuminated simultaneously or in a chosen pattern for a cycle of numbers. In this respect, the Kozak device is principally directed to the display of particular lights in response to the activation of particular switches, but no use is made of two or more switches to activate matching patterns of lights, nor are there any other functions performed by the device such as providing means for exercising the hands, fingers, etc.

As such, the prior art coordination teaching devices generally must be supplemented by other teaching aids if it is desired to increase the complexity of switch and light association or to provide means for exercising arm, hand, finger and eye muscles. In this connection, the present invention eliminates the need for providing additional teaching and exercising devices, thus fulfilling a long felt need in the industry.

SUMMARY OF THE INVENTION

The general purpose of the present invention is to provide a therapeutic teaching aid for individuals who have little or no control over their motor reflexes, eye coordination, or hand and finger muscle control through the use of a plurality of switch actuated colored lights and exercisers. In this respect, the present invention is designed to use a display panel as a reward system to encourage the use of the various switches, as well as a muscle-exercising slide device, in order to allow a student to regain the use of his muscle control and eye coordination. Specifically, the invention utilizes pushbutton, rotary, slide and toggle switches mounted on a housing and which may be selectively actuated to illuminate matching pairs of colored lights on the display panel in accordance with one mode of operation. Further, a centrally positioned slide is provided which serves to strengthen hand, finger and arm muscles while activating the lights on the display panel in accordance with another mode of operation. Also, rotary spring-loaded finger plate assemblies are located on respective sides of the housing for improving the coordination and muscle tone of a user's hands and fingers. The entire electrical assembly associated with the invention is housed in a vacuum formed plastic type housing or case that is designed to provide the maximum strength for operational handling of the unit and additionally, the entire assembly is supported by rubber vacuum cup feet so as to provide stability on any type of supporting surface. The electrical power supply cord is installed in a female socket on the machine thereby reducing the possibility of electrical shock, and the internal electrical supply is of low voltage, thus extending the operational life of the electrical components while reducing the maintenance costs associated therewith.

It is therefore an object of the present invention to provide a therapeutic aid which has all the advantages of the prior art therapeutic aids and none of the disadvantages and which may be easily and economically manufactured.

It is a further object of the present invention to provide a therapeutic aid that can be operated by untrained instructions, as well as trained therapists, with a minimum of instruction to thereby reduce training costs.

Still another object of the present invention is to provide a therapeutic aid that utilizes a variety of different types of switches for activating various colored lights in response to an actuation thereof.

Yet another object of the present invention is to provide a therapeutic aid that employs the use of a reward system for the proper sequencing of a plurality of switches associated therewith.

Even another object of the present invention is to provide a therapeutic aid that employs the use of exercising devices to improve muscle strength and tone.

A still further object of the present invention is to provide a therapeutic aid that utilizes an electrical assembly housed in a plastic case so as to assure maximum strength for operational handling of the aid.

Yet even another object of the present invention is to provide a therapeutic aid that is so constructed as to minimize the possibility of electric shock.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the therapeutic aid for the handicapped forming the present invention.

FIG. 2 is a transverse cross-sectional view of the present invention taken along the line 2—2 of FIG. 1.

FIG. 3 is a cross-sectional view of the slide assembly forming a part of the present invention and taken along the line 3—3 of FIG. 2.

FIG. 4 is a cross-sectional view of the digit exerciser assembly forming a part of the present invention and taken along the line 4—4 of FIG. 1.

FIG. 5 is a detailed structural view of a portion of the front panel forming a part of the present invention.

FIG. 6 is a transverse cross-sectional view of the slide assembly forming a part of the present invention and taken along the line 6—6 of FIG. 5.

FIG. 7 is a detailed structural view showing a portion of the back panel of the housing associated with the present invention.

FIG. 8 is a plan view of the backplate colorwheel utilized on the digit exerciser assembly of the present invention.

DESCRIPTION OF THE PREFERRED EMBODIMENT

Figure 9A:
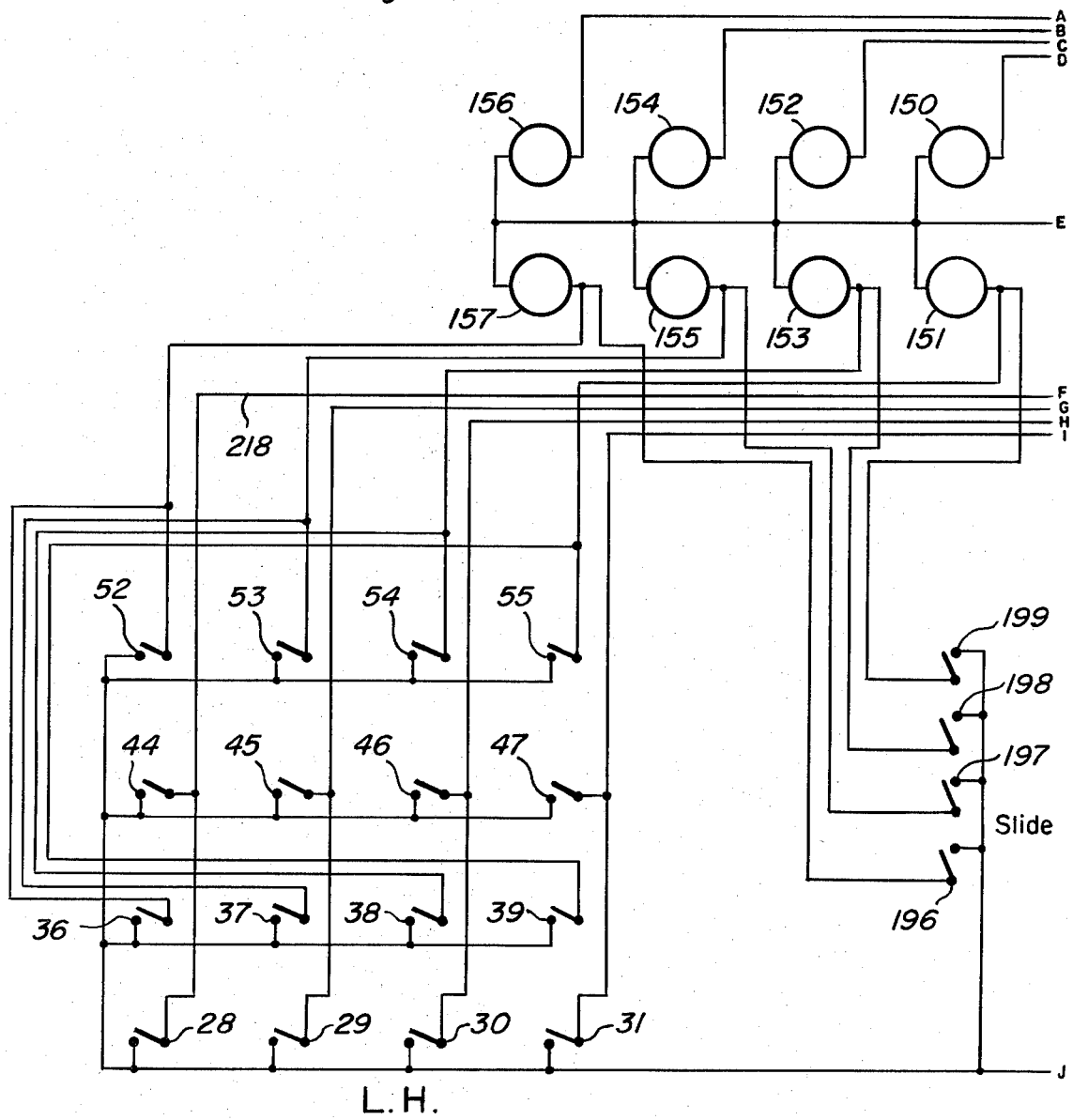
FIGS. 9a and 9b is the wiring schematic illustrating the electrical circuit associated with the operational parts of the present invention.

With reference now to the drawings and in particular to FIG. 1, there is shown a therapeutic aid for the handicapped embodying the principles and concepts of the present invention and generally designated by the reference numeral 10. In this respect, the therapeutic aid 10 includes a vacuum formed case or housing 12 having a plurality of various components operably attached thereto. Specifically, the housing 12 is of a basic rectangular shape including upwardly extending panels, i.e., front panel 14, back panel 16 and parallelly aligned side panels 18, 20, respectively. In this regard, the front panel 14, back panel 16, and side panels 18,20 are all integrally attached together since the housing 12 is of a molded plastic construction. Further, the housing 12 includes a top panel 22 on which a majority of the aforementioned electrical components are mounted, as well as an obliquely positioned view panel 24 integrally attached thereto and having a display panel 26 operably positioned therein.

With respect to the various components associated with the therapeutic aid 10, FIG. 1 further illustrates a plurality of pushbutton on/off switches 28–35, a plurality of rotary on/off switches 36–43, a plurality of slide on/off switches 44–51 and a plurality of toggle on/off switches 52–59. Further, a centrally positioned slide assembly 60 is illustrated, as is a rotary spring-loaded finger plate assembly 62.

An internal structural view of the therapeutic aid 10 is shown in FIG. 2 of the drawings, with the exception that the electrical connection wires for completing the electrical circuitry associated therewith have been left out for purposes of clarity. Specifically, it can be seen that the therapeutic aid 10 further includes a baseplate 64 connected to a bottommost portion of the housing 12. In this regard, it can be seen that the baseplate 64 is attachable to the housing 12 through the use of connection brackets 66, such brackets being attachable directly to the housing 12 through the use of conventional attachment means, such as rivets 68, and further being attachable to the baseplate by some conventional means such as screws 70. Further, spring clip nuts 72 might be positioned over the bracket 66 in the manner illustrated so as to effectively retain the screws 70 fixedly thereto. Additionally, rubber vacuum cups 74 may be attached to the baseplate 64 through the use of conventional attachment means, such as nuts 76 threadedly positionable over threaded studs 78 fixedly secured to the vacuum cups 74. As such, the vacuum cups 74 serve as cushioned support means for the therapeutic aid 10, while at the same time serving to prevent the aid from becoming easily displaced whereby the same might be dropped onto a surface resulting in damage thereto.

FIGS. 2 and 3 may be viewed together to understand the structural details of the slide assembly 60, such assembly including a knob 80, a slide cover 82, a guide slide 84 and a slide cam 86. As can be appreciated, the top panel 22 of the therapeutic aid 10 is provided with a slot 88 extending therethrough and into which the guide slide 84 associated with the slide assembly 60 is positioned. In this regard, the guide slide 84 is maintained in position within the slot 88 through the use of a threaded bolt 90 which serves to hold the knob 80, the slide cover 82, the guide slide 84 and the slide cam 86 altogether in an abutting relationship. Further, the slide cover 82 is of a width and length greater than the slot 88 whereby the slot is substantially at all times covered by the slide cover. Similarly, just as the slide cover 82 overlies a topmost portion of the top panel 22, the slide cam 86 is of a width and length greater than the slot 88 and overlies a bottommost portion of the top panel 22. Accordingly, the greater widths and lengths of the slide cover 82 and slide cam 86 prevent a disengagement of the slide assembly 60 from the top panel 22, while at the same time, a longitudinal movement of the slide assembly is permitted within the slot 88. In this respect, the guide slide 84 closely conforms in width to the width of the slot 88 while being of a substantially shorter length than the slot so as to facilitate the aforedescribed sliding movement of the slide assembly 60 as desired.

The slide assembly 60 further includes mounting brackets 92 and 94 which are centrally positioned with respect to the slide cam 86 and which are attached to the cam through the use of conventional attachment means, such as rivets 96, 98. The brackets 92, 94 are further respectively provided with apertures 100, 102 centrally positioned therein into which shoulder bushings 104, 106 may be respectively positioned in the manner illustrated. A third bracket 108 is longitudinally aligned with the brackets 92, 94 and is connected to the bottom side of the top panel 22 by some conventional attachment means such as rivet 110. The bracket 108 also has a central aperture 112 into which is positioned a further shoulder bushing 114. In this connection then, a longitudinally extending slide rod 116 may be directed through the three apertures 100, 102, 112 in a manner where it is securely positioned within the respective shoulder bushings 104, 106 and 114. The slide rod 116 includes a threaded portion 118 onto which a pair of nuts 120, 122 and washer 124 may be positioned. A second washer 126 may be further positioned over the rod 116 and a compression spring 128 may be positioned between the respective washers 124, 126 in a manner which permits the slide rod 116 to extend therethrough. In this respect, it can be appreciated that the slide rod 116 is fixedly secured in position relative to the bracket 108 by any conventional means, so that a forward movement of the slide assembly 60 will result in the bracket 92 causing a forcible compression of the spring 128, thereby continually increasing the compression force associated with moving the slide assembly upwardly on the top panel 22 towards the display panel 26. By the same token, the two nuts 120, 122 may be threadedly moved along the threaded portion 118 of the slide rod 116 so as to vary the compression force on the spring 128, thereby to increase or decrease the amount of force associated with an upward movement of the slide assembly 60 toward the display panel 26.

Further illustrated in FIG. 2 is a diffuser assembly 130 which includes a plastic diffusion plate 132, which effectively forms the display panel 26 shown in FIG. 1, and a lamp mounting plate 134. A plurality of spacers 136 are positioned between the diffusion plate 132 and the lamp mounting plate 134 in the manner illustrated, such spacers 136 preferably consisting of ¼ inch inside diameter plastic or metal tubing and having a plurality of flathead machine screws 138 positioned therethrough. In this respect, nuts 140 may be utilized to secure the lamp mounting plate 134 into operable association with the diffusion plate 132 and being spaced therefrom by the length of the individual spacers 136. Mounted to the lamp mounting plate 134 are a plurality of miniature bayonet sockets 141, such sockets being of a conventional construction and serving to retain one of a plurality of miniature lamps 142-157 therein. In this regard, the lamps 142-157 are of the bayonet base type and may be of either a clear or colored construction. In the preferred embodiment illustrated, it is envisioned that the lamps 142, 143 might be of a yellow color, lamps 144 and 145 of a red color, lamps 146 and 147 of an orange color, lamps 148 and 149 of a purple color, lamps 150 and 151 of a blue color, lamps 152 and 153 of a green color, lamps 154-155 of a violet color, and lamps 156 and 157 of a light blue color. Of course, it is to be understood that any combination of colors might be utilized without departing from the scope or intent of the present invention. Further, it can be appreciated that the lamps 142-157 are aligned in two parallel rows extending along the length of and beneath the display panel 26. As such, only lamps 150 and 151 are visible in the drawing of FIG. 2.

Further illustrated in FIG. 2 are some of the constructional details of the digit exerciser assembly 62. In this respect, it is to be realized that two substantially identical digit exerciser assemblies 62 are provided, one of which is mounted on the side panel 18 and the other of which is mounted on the side panel 20 of the therapeutic aid 10. Viewing FIG. 4 in conjunction with FIG. 2, it can be seen that the respective digit exerciser assemblies 62 are mountable through a pair of apertures 158, one of which is in each of the respective sidewalls 18, 20. Further, the digit exerciser assembly 62 is retained in position within the respective apertures 158 through the use of mounting brackets 160, such brackets being retained in a fixedly secured position against the respective sidewalls through the use of conventional attachment means such as rivets 162. With particular reference to the digit exerciser assembly 62 positioned in the sidewall 20, as shown in FIGS. 2 and 4, it can be seen that the assembly further includes a finger plate 164, which might be of a metal or opaque plastic construction and which has a plurality of apertures 166 contained therein into which a user's fingers may be inserted. Further, the finger plate 164 is in an abutting relationship with a back plate color wheel 168, which might also be of a metallic or clear plastic construction, but which in the preferred embodiment is of a construction similar to that shown in FIG. 8. Specifically, the backplate color wheel 168 shown in FIG. 8 illustrates the fact that various colors may be positioned behind each of the six illustrated apertures 166 associated with the finger plate 164, so as to further enhance the eye coordination and attractiveness of the present invention.

Referring again to the construction of the digit exerciser assembly 62 as illustrated in FIGS. 2 and 4, it can be further seen that the mounting bracket 160 is provided with a centrally positioned aperture into which is inserted a threaded bushing 170, such bushing being fixedly secured to the bracket 160 by conventional attachment means such as by silver soldering or the like, and a threaded shaft 172 is then screwably inserted through the bushing 170. The shaft 172 is further directed through centrally positioned apertures within the backplate color wheel 168 and the finger plate 164 so that an acorn nut 174, along with a washer 176, may be utilized to secure the assembly in position as illustrated in FIG. 4. To prevent the backplate color wheel 168 and the finger plate 164 from moving inwardly along the shaft 172, a compression spring 178 is provided, and as can be appreciated, the spring constant or the distance between the threaded bushing 170 and the backplate color wheel 168 may be varied as desired to increase the amount of strength required by the user to effectively rotate the finger plate. As such, the tension associated with rotating the finger plate 164 is accurately and selectively adjustable.

Viewing FIG. 2 in conjunction with FIGS. 5 and 6, even further constructional details relating to the operation of the slide assembly 60 can be ascertained. With particular reference to FIGS. 5 and 6, it can be seen that the slide assembly 60 lies proximate to two roller switch assemblies 180, 182. In this connection, the respective roller switch assemblies 180, 182 are mounted on opposite sides of the longitudinal slot 88 and are retained in position through the use of brackets 184, 186, respectively. As shown, bracket 184 is secured to the casing 12 by some conventional attachment means, such as by a plurality of rivets 188, only one of which is shown, while bracket 186 is similarly secured to the casing by a plurality of rivets 190. Further, the roller switch assembly 180 is secured to the bracket 184 through the use of a conventional attachment means, such as a plurality of machine screws and nuts 192, only one of which is shown, while roller switch assembly 182 is mounted to bracket 186 by a plurality of similar screws 194 or the like.

As can be particularly ascertained with reference to FIG. 6, the roller switch assembly 180 includes the use of at least four roller spring switches 196-199, only 196 and 197 of which can be seen, such switches being mounted in tandem pairs as can be further ascertained with particular reference to FIG. 2. In this respect, roller spring switch 199 can be viewed in FIG. 2 and it is to be understood that a similar roller spring switch 198 is tandemly mounted beside the switch 199 in the manner of switches 196 and 197 as shown in FIG. 6. Similarly, at least four other roller spring switches 200-203 are associated with the roller switch assembly 182 in the same manner that switches 196–199 are associated with the assembly 180. In this connection, roller spring switches 200 and 201 can be viewed in FIG. 6 and it is to be understood that switches 202 and 203 are similarly mounted and lie behind switches 200 and 201.

As can be appreciated with reference to FIGS. 2, 5 and 6, a forward movement of the slide assembly 60 toward the display panel 26 will result in the slide cam 86 sequentially coming into contact with the various roller spring switches 196–203 so as to effectively close the circuits associated with each of the individual switches. Specifically, it can be seen that the slide cam 86 is provided with a forward upward sloping cam surface 204 which establishes initial contact with each of the rollers associated with the respective switches 196–203, so as to forcibly and gradually cause a downward movement of the respective roller spring switches to close the associated electrical circuits.

Referring again to FIG. 2 in conjunction with FIG. 7, it can be seen that the back panel 16 of the housing 12 is provided with a toggle on/off switch 206 mounted therein which controls the delivery of electrical power to the therapeutic aid 10. Additionally a female electrical socket 208 is provided so as to facilitate the delivery of electrical power to the therapeutic aid 10. With particular reference to FIG. 7, it can be further seen that a pilot lamp 210 may be provided on the back panel 16 as a means of indicating when electrical power is being delivered to the therapeutic aid 10. In this regard, when the toggle switch 206 is on, so as to activate the electrical circuit associated with the invention, the pilot lamp 210 will be lit and conversely, when the toggle switch 206 is in the off position, thereby preventing a delivery of electrical power to the circuit, the pilot lamp 210 will be turned off.

Figure 9B:
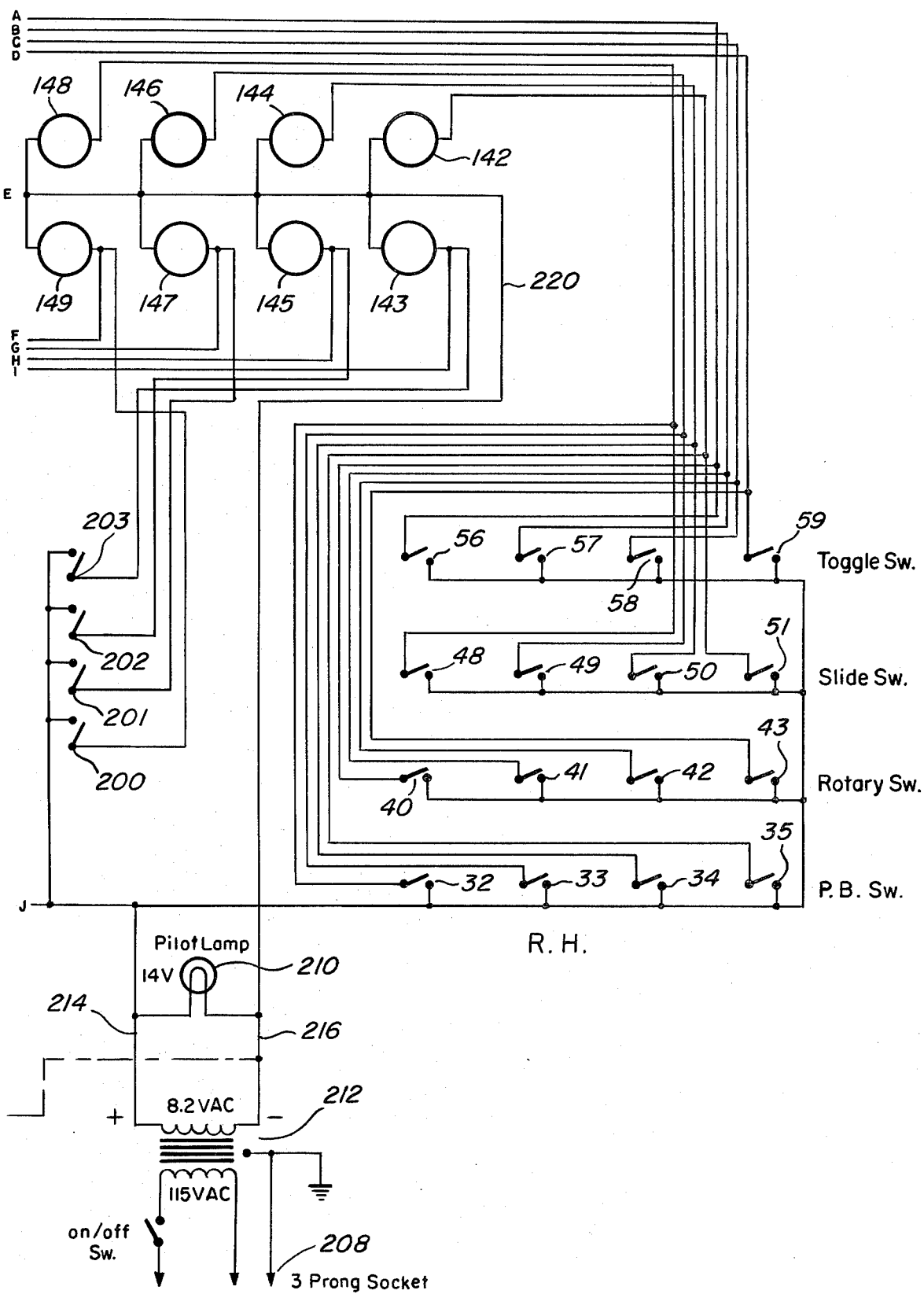

FIGS. 9a and 9b must be viewed in conjunction to understand one preferred embodiment of the electrical circuitry which may be utilized to operate the therapeutic aid 10. In this connection, it can be appreciated that the ends of the respective electrical leads A–J as illustrated in FIG. 9a are integrally attached to and a part of the similarly lettered ends of electrical leads A–J illustrated in FIG. 9b. As such, the wiring schematic illustrated in FIGS. 9a and 9b is to be viewed in combination as simply one schematic which by necessity had to be placed on two different sheets of drawings. In this respect, it can be seen that the three-prong electrical socket 208 supplies power to a filament transformer 212 so as to provide for low voltage operation within the therapeutic aid 10. Further illustrated is the pilot lamp 210 having one lead associated therewith in electrical connection with the positive lead 214 directed from the transformer 212 and having its other lead directed to a ground or negative lead 216. As such, a plurality of series circuits are provided which are effectively opened and closed by the respective plurality of switches above discussed, such circuits all serving to operate one or more of the lamps 142–157. For example, it can be seen that a closing of the pushbutton switch 28 will permit a flow of current through lead 218 to lamp 149 which is then connected to ground by means of lead 220. Accordingly, a user will be rewarded by a depression of the pushbutton switch 28 with an indication of his having successfully done so through the illumination of lamp 149, which as aforementioned might be of a purple color. In this respect, it can be seen that each of the left-hand pushbutton switches 28–31 and the right-hand pushbutton switches 32–35 will individually light certain ones of the lamps 142–157. For example, pushbutton switch 29 will illuminate lamp 147, pushbutton switch 30 illuminates lamp 145, and pushbutton switch 31 illuminates lamp 143. By the same token, the right-hand pushbutton switch 32–35 will respectively illuminate lamps 148, 146, 144 and 142. Accordingly, the particular circuit arrangement illustrated with respect to the pushbutton switches 28–35 effectively controls the lighting of lamps 142–149, all of which may be positioned wherever desired behind the display panel 26. Further, the pushing of certain pairs of switches will result in similarly colored bulbs being illuminated. For example, switches 28 and 32 control the purple lamps 148, 149, while switches 29 and 33 control the orange lamps 146, 147. Similarly, switch pairs 30, 34 and 31, 35 control red lamps 144, 145 and yellow lamps 142, 143, respectively.

As an additional feature of the present invention, each of the pushbutton switches 28–35 are respectively associated with a slide switch 44–51 in a manner whereby the closing of either one or the other will result in the lighting of the associated lamp 142–149. For example, in lieu of closing pushbutton switch 28, a user might choose to activate slide switch 44 so as to effect a lighting of the purple lamp 149. Similarly, slide switch 45 may be utilized in place of pushbutton switch 29 to effect a lighting of the lamp 147. By the same token, slide switches 46–51 are respectively interchangeable with the pushbutton switches 30–35, and this construction provides for a different type of motor movement by a user so as to effectively illuminate the lamps 142–149.

Following the same line of logic, the rotary switch 36 may be closed by a user to effectively light the light blue lamp 157, while alternatively the toggle switch 52 may be activated to light the same lamp. For a user to illuminate the second light blue lamp 56, it is necessary that he activate alternatively the rotary switch 40 or the toggle switch 56 associated therewith. Similarly, rotary switches 37–39 which are manipulatable by a user's left hand are respectively associated with the toggle switches 53–55 to respectively light the lamps 155, 153 and 151. As to a user's right hand, rotary switches 41–43 are respectively associated with toggle switches 57–59 and may be manipulated by a user to illuminate lamps 154, 152 and 150 respectively. As such, a handicapped or other person has a number of alternative switches provided which require different motor movements for illuminating a plurality of brightly colored lamps 142–157. In this connection, it is to be understood that many various color combinations of lamps 142–157 may be provided behind the display panel 26, while the various types of switches may be conventionally connected to the lamps in many different patterns to achieve the desired coordination and muscle tone training of an individual.

FIGS. 9a and 9b further illustrates the positioning and use of the roller spring switches 196–203. Specifically, it can be appreciated that the roller spring switches 196–203 are sequentially closed through a movement of the aforedescribed slide assembly 60 and serve to indicate to a handicapped or other person the extent of movement of the slide that he has achieved. For example, a partial movement of the slide assembly 60 in a forward direction will initially result in a closing of the switches 196, 197, 200 and 201, thereby to illuminate lamps 157, 155, 149 and 147. If the user possesses enough strength to move the slide assembly further along the slot 88, he will be rewarded with a closing of switches 198, 199, 202 and 203 thereby to illuminate further lamps 153, 151, 145 and 143. In other words, a complete forward movement of the slide assembly 60 will result in an illumination of eight of the sixteen lamps contained behind the display panel 26. Again, it should be noted that the lamps 142-156 may be arranged in any desired manner and color pattern which is aesthetically pleasing, while the circuit diagram shown in FIGS. 9a and 9b may be varied in a conventional manner to change the lighting sequence of the lamps.

Figure 10:
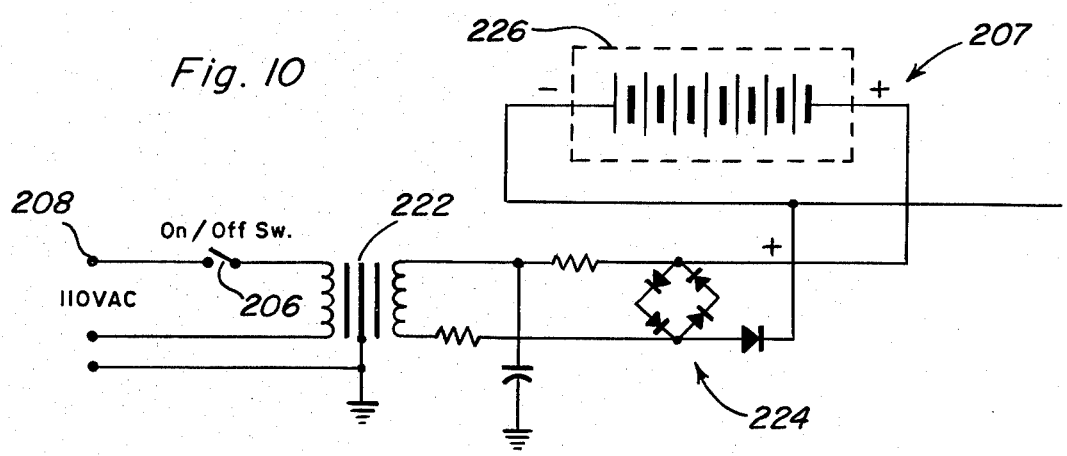
FIG. 10 is a wiring schematic illustrating the optional rechargeable battery pack which may be utilized with the present invention.

FIG. 10 has been provided to illustrate an optional power pack 207 which may be utilized in combination with the present invention. Specifically, FIG. 10 illustrates an incoming power supply directed to socket 208 in combination with the on/off toggle switch 206. A transformer 222 may be utilized to step down the voltage provided to a rectifying circuit 224 which effectively converts the alternating current to direct current, this current then being suppliable to a Nicad rechargeable battery 226 which may be used to power the circuitry of the present invention if desired. In this respect, the alternating current to direct current converter circuit illustrated in FIG. 10, including the rechargeable battery 226, is of a conventional construction and no further discussion with respect thereto will be provided.

In use then, it can be seen that the therapeutic aid 10 is effective in developing hand and eye coordination, as well as being effective in developing muscle tone in a user's fingers, wrists, forearms, etc. In this respect, a user may develop his hand and eye coordination by activating any one of the plurality of switches 28-59 which in turn illuminates one or more of the variously colored lamps 142-157. In this connection, the use of various types of switches requires different motor movements on the part of the user, including pushing movements, turning and twisting movements, sliding movements, and shoving or grasping movements. Further, a user is afforded the opportunity to exercise and develop his muscles through the use of the slide assembly 60, whereby the user may grasp the knob 80 associated with the slide assembly and then force the slide assembly towards the display panel 26 against an increasing spring force afforded by the compression spring 128. If the user succeeds in pushing the slide assembly 60 completely forward, he will be rewarded with eight colored lamps flashing on, while a lesser amount of lamps will be illuminated if the slide assembly is not pushed all the way forward. Additionally, a user may insert his fingers into one of the digit exerciser assemblies 62 and may then effect a rotation thereof against a spring tension force afforded by compression spring 171.

As such, it can be appreciated that the present invention has been developed to provide therapeutic exercise for the individual who has little or no control over his motor reflexes, eye coordination, or hand and finger muscle activity. Additionally, the present invention serves as an exerciser to develop the muscle control necessary for normal human functioning. The aforedescribed reward system creates work incentive in a user through the use of an assortment of commonly used electrical switches in conjunction with the display panel of colored electric lamps. As above described, the coordination is provided by the matching of colors between the lamps and switches. By encasing the entire electrical assemblies in a vacuum formed case made of ABS plastic material, maximum strength for operational handling of the unit is provided. Further, through the use of rubber suction cup feet, the assembly is stable on any type of supporting surface and slippage is prevented on hard or slippery surfaces.

Another advantage is that the electrical power cord is installed in a female socket on the machine thereby reducing the possibility of electrical shock. In this respect, all of the electrical circuits are designed for low voltage operation wherein the power is supplied by a filament transformer that is operated by a 110 volt alternating current electric supply. The power cord is connected to the case by inserting the cord into a recessed female plug to avoid any possible electric shock, and an optional power source can be supplied by using the aforementioned rechargeable Nicad battery packs with built-in chargers in lieu of the transformer. Both the lamp assemblies and switches are rated for higher voltage use therefore extending their respective operating lives.

As can be further appreciated, the present invention was developed to be used by non-professional teachers, as well as trained therapists, with a minimum of instruction thereby reducing training costs. In this respect, no previous skill is required to use the present invention in a teaching environment, and the rate of the student instruction can be entirely controlled by the instructor to match the student's comprehension and agility. Further, the device can be used by adults and children alike and provides a way for the untrained teacher, as well as the therapist, to control the training process.

With respect to the above description of the preferred embodiment, it should be realized that the optimum dimensional relationships for the parts of the present invention are deemed readily apparent and obvious to one skilled in the art, and all equivalent relationships to those illustrated in the drawings and described in the specifications are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A therapeutic aid for developing hand and eye coordination of a user, said aid comprising:
   a housing;
   switch means mounted on said housing, said switch means being selectively actuatable by said user;
   display means mounted on said housing and being operable in response to an actuation of said switch means by said user;
   exercise means mounted on said housing and being selectively actuatable by said user for purposes of improving said user's muscle control and strength; and
   power supply means for energizing said display means in response to actuation of one of said switch means and the exercize means.

2. The therapeutic aid for developing hand and eye coordination of a user as defined in claim 1, wherein said display means includes at least one lamp which is illuminable in response to said actuation of said switch means.

3. The therapeutic aid for developing hand and eye coordination of a user as defined in claim 1, wherein said switch means includes at least two different types of switches which may be operated to activate said display means.

4. The therapeutic aid for developing hand and eye coordination of a user as defined in claim 1, wherein said exercise means includes a slide assembly for developing muscle control and strength of said user.

5. The therapeutic aid for developing hand and eye coordination of a user as defined in claim 4, wherein said exercise means further includes a digit exerciser assembly for exercising said user's hand and finger muscles.

6. The therapeutic aid for developing hand and eye coordination of a user as defined in claim 1, wherein said display means includes a plurality of colored lamps selectively illuminable in response to said actuation of said switch means.

7. The therapeutic aid for developing hand and eye coordination of a user as defined in claim 1, wherein said switch means includes the use of pushbutton switches, rotary switches, slide switches and toggle switches selectively actuatable by a user to operate said display means.

8. The therapeutic aid for developing hand and eye coordination of a user as defined in claim 7, wherein said display means includes a plurality of colored lamps selectively illuminable in response to said actuation of said switches.

9. A therapeutic aid for developing hand and eye coordination of a user, said aid comprising:
a housing;
switch means mounted on said housing, said switch means being selectively actuable by said user;
display means mounted on said housing and being operable in response to an actuation of said switch means by said user;
exercise means mounted on said housing and being selectively actuatable by said user for purposes of improving said user's muscle control and strength; and
power supply means for energizing said display means in response to at least an actuation of said switch means, said display means including a plurality of colored lamps selectively illuminable in response to said actuation of the switch means, said plurality of colored lamps also being selectively actuatable in response to a movement of said exercise means.

10. A therapeutic aid for developing hand and eye coordination of a user, said aid comprising:
a housing;
switch means mounted on said housing, said switch means being selectively actuatable by said user;
display means mounted on said housing and being operable in response to an actuation of said switch means by said user;
exercise means mounted on said housing and being selectively actuatable by said user for purposes of improving said user's muscle control and strength; and
power supply means for energizing said display means in response to at least an actuation of said switch means, said switch means including the use of pushbutton switches, rotary switches, slide switches and toggle switches selectively actuatable by a user to operate said display means, said display means including a plurality of colored lamps selectively illuminable in response to said actuation of said switches, various combination of said pushbutton switches, rotary switches, slide switches and toggle switches are utilized to illuminate respective ones of said plurality of lamps contained in said display means so as to permit an illumination of a same lamp by two or more different switches.

11. A therapeutic aid for developing hand and eye coordination of a user, said aid comprising:
a housing;
switch means mounted on said housing, said switch means being selectively actuatable by said user;
display means mounted on said housing and being operable in response to an actuation of said switch means by said user;
exercise means mounted on said housing and being selectively actuatable by said user for purposes of improving said user's muscle control and strength; and
power supply means for energizing said display means in response to at least an actuation of said switch means, said exercise means including a slide assembly for developing muscle control and strength of said user, said slide assembly serving to operate said display means in response to an actuation thereof by a user.

12. A therapeutic aid for developing hand and eye coordination of a user, said aid comprising:
a housing;
switch means mounted on said housing, said switch means being selectively actuatable by said user and including a plurality of pushbutton switches, rotary switches, slide switches and toggle switches;
display means mounted on said housing and being operable in response to an actuation of said switch means by said user, said display means including a plurality of variously colored lamps in selective electrical communication with said switch means;
exercise means mounted on said housing and being selectively actuatable by said user for purposes of improving said user's muscle control and strength, said exercise means including a slide assembly operable to actuate said display means in response to a movement thereof, and further including a digit exerciser assembly for improving muscle control and strength in a user's hands and fingers; and
power supply means for energizing said display means in response to an actuation of one of said switch means and said slide assembly.

13. A therapeutic aid for developing coordination comprising a housing, a plurality of manually operable switch devices mounted on the housing for selective actuation thereof, display means mounted on the housing and operatively connected to the switch devices for operation in a first mode in response to said actuation of the switch devices, exercise means mounted in the housing for manual manipulation, and means operatively connecting the exercise means to the display means for operation thereof in a second mode in response to said manual manipulation of the exercise means.

14. The combination of claim 13 wherein said display means includes a plurality of lamps illuminated in different patterns indicating the switch devices actuated in accordance with said first mode of operation, and illuminated in accordance with the second mode of operation to indicate the degree of manipulation of the exercise means.

* * * * *